United States Patent [19]
Dimarogonas

[11] Patent Number: 5,836,891
[45] Date of Patent: Nov. 17, 1998

[54] METHOD AND APPARATUS FOR DETERMINING THE DENSITY AND STRUCTURAL INTEGRITY OF BIOLOGICAL TISSUES, MEDICAL IMPLANTS AND STRUCTURAL PARTS

[76] Inventor: Andrew D. Dimarogonas, 7135 Pershing Ave., St. Louis, Mo. 63130

[21] Appl. No.: 859,439

[22] Filed: May 20, 1997

[51] Int. Cl.⁶ ........................................ A61B 5/00
[52] U.S. Cl. ................... 600/552; 600/553; 600/587
[58] Field of Search ..................... 600/552, 553

[56] References Cited

U.S. PATENT DOCUMENTS

| | | |
|---|---|---|
| 3,482,486 | 12/1969 | Nordhelm, Jr. . |
| 3,509,734 | 5/1970 | Lederer . |
| 3,815,407 | 6/1974 | Laverey . |
| 4,006,626 | 2/1977 | Ruzicka et al. . |
| 4,031,744 | 6/1977 | Flannelly . |
| 4,289,023 | 9/1981 | Rader . |
| 4,342,229 | 9/1981 | Massa . |
| 4,526,465 | 7/1985 | Corti et al. . |
| 4,641,527 | 2/1987 | Hiroi et al. . |
| 4,723,448 | 2/1988 | Veligdan . |
| 4,754,763 | 7/1988 | Doemland ............................... 600/552 |
| 4,799,498 | 1/1989 | Collier .................................. 600/552 |
| 4,823,601 | 4/1989 | Barna . |
| 4,824,250 | 4/1989 | Newman . |
| 4,928,527 | 5/1990 | Burger et al. . |
| 5,006,984 | 4/1991 | Steele . |
| 5,227,982 | 7/1993 | Kipple et al. . |
| 5,245,862 | 9/1993 | Zeiss . |
| 5,402,781 | 4/1995 | Dimarogonas ........................ 600/552 |
| 5,432,834 | 7/1995 | Gershman . |
| 5,476,009 | 12/1995 | Dimarogonas . |
| 5,484,388 | 1/1996 | Bassett et al. ........................ 601/27 |
| 5,594,775 | 1/1997 | Hangartner . |
| 5,602,486 | 2/1997 | Novak . |
| 5,603,325 | 2/1997 | Mazess et al. . |

*Primary Examiner*—Max Hindenburg
*Assistant Examiner*—Pamela L. Wingood
*Attorney, Agent, or Firm*—Paul M. Denk

[57] ABSTRACT

A non-destructive and non-invasive method and apparatus determines the structural integrity of discrete pieces of material, such as bone, medical implants and structural parts by determining the impact ratio of a striking mass that impacts and rebounds from the material. The impact ratio is equal to the ratio of instantaneous velocity of the striking mass immediately after the impact to the instantaneous velocity of the striking mass immediately prior to impact. A means can be used to force the striking mass towards the material to impact the material. In this case, the measured history of the displacement during the impact and the rebound are used to compute the impact ratio, the ratio being directly related to the impact reaction of the material. The impact ratio can be used to determine the structural integrity of the material or the onset of osteoporosis. The impact ratio can also be compared with previous measurements of the same piece of material or with standardized values of impact ratios to monitor changes in the impact reaction of the discrete piece of material for the diagnosis of incipient failure in the material and monitor the structural integrity of the piece of material.

28 Claims, 2 Drawing Sheets

METHOD AND APPARATUS FOR DETERMINING THE DENSITY AND STRUCTURAL INTEGRITY OF BIOLOGICAL TISSUES, MEDICAL IMPLANTS AND STRUCTURAL PARTS

CROSS-REFERENCE TO RELATED APPLICATIONS

Not applicable

STATEMENT REGARDING FEDERALLY SPONSORED RESEARCH OR DEVELOPMENT

Not applicable.

BACKGROUND OF THE INVENTION

1. Field of the Invention

The present invention relates to a non-destructive and non-invasive method and apparatus for the determination and monitoring of the structural integrity of bones and other biological tissues, medical implants and structural parts. More specifically, the impact density and the impact parameters of the material to be tested is determined by an impact of a predetermined speeding mass with the material to be tested and continuous measurements of the position and velocity of the impacting mass.

2. Background

Knowledge of the mechanical properties of biological tissues such as bones, teeth, nails, hair, muscles, etc., to be called hereafter "tissues", is important in monitoring their structural integrity and in diagnosis and monitoring of abnormal medical condition of the tissues. For example, studies of bone strength have demonstrated that decreases in bone strength in both the spine and femur are directly proportional to bone mineral content, and mechanical properties such as modulus of elasticity and vibration damping. For the first effect, bone densitometry has been used extensively for the determination of bone loss in clinical diagnosis and monitoring. A variety of methods have been used, such as single and dual photon absorptiometry and quantitative computer tomography (Gershman; Russell J., U.S. Pat. No. 5,432,834, Hangartner; Thomas N., U.S. Pat. No. 5,594,775). Modulus of elasticity is measured with the aid of the delay and attenuation of ultrasonic waves or by dynamic impedance measurements (Mazess; Richard B. Wiener; Scott A., U.S. Pat. No. 5,603,325, Steele, U.S. Pat. No. 5,006,984) and damping is measured by the analysis of the damped resonant response of the bone (Dimarogonas, U.S. Pat. No. 5,402,781). However, these methods are time-consuming, dependent upon the availability of sophisticated and expensive equipment, and thus expensive and difficult for widespread implementation. As a result there has been long-felt need in the art for a simple, efficient, and low cost methodology for measuring bone impact reaction, as impact reaction is an effective indicator of the density and the structural integrity of a tissue, for example of the onset of osteoporosis in bones, a debilitating disease commonly found in post-pregnancy and post-menopausal women. Treatment of osteoporosis and other illnesses is most effective if the disease is detected early whereupon treatment may be commenced. However, because of the increased risk of side effects, it is undesirable to begin treatment until the disease has been detected. Additionally, measurement of tissue impact reaction over time may be used to determine the effectiveness of treatment, leading to adjustments in the treatment protocols balanced against the attendant side effect risk.

In addition to the measurement of the tissue density, modulus of elasticity and vibration damping as means of diagnosing tissue illness have also been proposed in the literature and the prior art.

All three methods above, give an average of the respective mechanical properties over the whole tissue or over a large part of it and cannot be used for local measurements at different points on the tissue that are known to be points where malfunction is usually initiated.

Medical implants are sometimes rejected by the body either due to the failure of the implant itself or the deterioration of the surrounding tissue. Usually the failure of the implant remains undetected until it is too late because of the lack of sensitive monitoring methods.

Structural parts, such as machine parts, structural elements of bridges, aircraft, nuclear reactors and other structures often degrade and fail. If not detected early, the part failure could lead to a catastrophic failure of the structure. If the incipient failure is detected early, the part can be repaired or replaced without damage of the integrity of the structure. The need to assess the structural integrity of structural parts has prompted substantial research and development work in the field of non-destructive testing of materials.

Methods based in the vibration analysis of the structural part or the propagation of ultrasonic waves, or the penetration by radiation beams have been disclosed (for example, Neish et al, U.S. Pat. No. 3,482,486; Avery, U.S. Pat. No. 3,815,407; Flannelly, U.S. Pat. No. 4,031,744; Massa, U.S. Pat. No. 4,342,229; Corti et al, U.S. Pat. No. 4,526,465; Hiroi et al, U.S. Pat. No. 4,641,527; Veligdan, U.S. Pat. No. 4,723,448; Barna, U.S. Pat. No. 4,823,601; Newman, U.S. Pat. No. 4,824,250, Burger et; U.S. Pat. No. 4,928,527; Kipple et al, U.S. Pat. No. 5,227,982; Dimarogonas, U.S. Pat. No. 5,476,009; and Novak, U.S. Pat. No. 5,602,486).

All methods in the previous art require extensive instrumentation, they are laborious and in many applications they are either difficult to use or simply too expensive.

The need for advanced, yet more practical and simple, methods of non-destructive and non-invasive testing of bones, other biological tissues, medical implants and structural parts can be addressed with the present invention of a new method and apparatus based on the performance of the above materials during an impact with a speeding mass.

Mechanics of impact of solids, the study of motion of two bodies that collide as a speeding mass, to be called hereafter "striking mass", impacts on another mass that might be stationary or moving, to be called hereafter "stricken mass", is well documented (see, for example: Housner, G. W., Hudson, D. E., *Applied Mechanics-Dynamics*, D. Van Norstand Co., New York, 1950).

There are impact methods to measure an impact property of a striking mass as it rebounds on a stricken mass, in particular on the surface of an immovable body, the restitution coefficient. For example, Zeiss (U.S. Pat. No. 5,245,862) estimated the restitution coefficient by measuring the bounce periods between impacts of a ball as it bounces on a flat rigid surface.

Another method of measuring the impact property of a striking mass is taught by Saari (U.S. Pat. No. 3,509,734) who measures the restitution coefficient of tennis balls by measuring the travel time of a ball dropped from a predetermined height on a flat rigid surface.

A second method of measuring the impact property of a striking mass was taught by Ruziscka et al. (U.S. Pat. No. 4,006,626) who measure the restitution coefficient by measuring the rebound height of a ball dropped from a predetermined height on a flat rigid surface.

In the prior art, the restitution coefficient was not affected measurably by the mass of the stricken body that was rigidly connected to the ground. Thus the measured restitution coefficient was relative insensitive to the density of the stricken object.

BRIEF SUMMARY OF THE INVENTION

In order to solve these and other problems, I have developed a method and apparatus for determining the impact reaction by measuring the ratio of the rebound velocity over the impact velocity, termed "impact velocity ratio (IVR)", of a predetermined mass, to be called hereafter "the striking mass", as it impacts a resiliently supported tissue or other material, a measure of the tendency of a mass to rebound after impact with a resiliently supported tissue or another material, to be called hereafter "the stricken mass". For example, the bones of osteoporotic persons usually break due to a sudden motion or impact and thus the impact velocity ratio (IVR) is directly related with impact on the bone. While the impact velocity ratio (IVR) is affected by the bone material density, elasticity, viscoelasticity and inelasticity, it is a measure of the overall ability of the bone to resist impact, thus is a better indicator for the bone impact reaction that is related with osteoporosis.

In general, I developed a technique for measuring the impact velocity ratio (IVR) of a predetermined mass as it impacts any bone or other biological tissue or medical implant or structural part. This technique consists of tapping the particular point of interest on the tissue or material, in general, with a light, instrumented striking mass, in the preferred embodiment a medical hammer, and measuring the approach and rebound velocities. A variety of methods exist for the continuous measurement of the velocity of a moving mass. In the preferred embodiment, a transducer affixed permanently to the striking mass senses the motion and produces an electrical output which is proportional to the hammer motion. A recorder or a programmed electronic logic device such as a computer may be used to determine the impact velocity ratio (IVR) from the electrical output of the transducer.

In the first implementation of this method, an impact or a number of impacts of a striking mass is applied to the stricken mass, such as by striking the stricken mass with the instrumented hammer, in order to generate a rebound of the striking mass. This motion of the striking mass has a maximum velocity at exactly the time the striking mass first contacts the stricken mass, to be called hereafter "impact velocity", and a different maximum velocity as the striking mass rebounds away from the stricken mass at exactly the time that the striking mass loses contact with the stricken mass, to be called hereafter "rebound velocity". The two velocities measured are used to calculate the impact velocity ratio (IVR). In a second implementation of this same method, an actuator-driven mass is made to impact the tissue, in the preferred embodiment by release of a preloaded spring. The velocity of the mass as it approaches the tissue just prior to impact and when it rebounds away from the tissue is recorded and from this the impact velocity ratio (IVR) can be computed.

Furthermore, although it is desirable to locate the impact point close to the tissue in order to increase the gain of the measured velocity and decrease noise from other tissues to thereby minimize measurement errors, it has been found that in the case of bone, the soft tissue which surrounds the bone has little affect on the measurement because the bone dominates the rebound energy. Thus, the impact can be administered on the skin and the measurements may be taken through the soft tissue surrounding the bone. Thus, no penetration of the skin is required to make the measurement.

Still further, as the impact velocity ratio (IVR) is a local measure of the transfer of kinetic energy to the tissue and the loss of strain energy during restitution, it is relatively insensitive to boundary conditions such as the soft support under the tissue and the characteristics of the surrounding bones or soft tissue. On the other hand, other dynamic properties, such as the natural frequency and the vibration damping factor, might vary when the boundary conditions change, and are not nearly as sensitive to changes in impact reaction, which makes impact velocity ratio (IVR) a superior indicator to use in measuring and monitoring tissue impact reaction and changes of it over time.

Experiments have supported my conclusion that the impact velocity ration (IVR) is indicative of bone density, and that the smaller the IVR, the lower the bone density. It is generally understood and believed that loss of mass, or decrease in impact reaction, of a hard tissue, such as a bone, is due to the loss of minerals and a resultant void nucleation that, in turn, results in stress concentration and premature fracture or malfunction. This void nucleation is detected by a change in the impact velocity ratio (IVR) as the bone becomes more porous which decreases the bone density and stiffness and increases the bone inelasticity. Thus, the measurement of the impact velocity ratio (IVR) is seen to be a direct measurement of the structural effect of this void nucleation and, hence, a direct indication of the impact reaction of the bone.

My techniques may be readily applied to the diagnosis and treatment of osteoporosis. In the first instance, the impact reaction of a particular bone of a patient may be estimated by measuring the impact velocity ratio (IVR), and the impact velocity ratio (IVR) may be determined in the same manner at various intervals of time as the patient is treated. These impact velocity ratios (IVR) that are taken at various time intervals may be compared to detect any changes which would indicate a change in bone impact reaction. A decrease in bone impact reaction in medically significant amounts indicates the onset of osteoporosis. Alternately, it would be hoped that treatment, perhaps through exercise, or the administration of estrogens or other drugs would be helpful in increasing or at least forestalling the decrease in bone impact reaction. Thus, these techniques may be useful in measuring the effectiveness of treatments so that treatment protocols may be altered over time as the patient is treated. This methodology and use of the impact velocity ratio (IVR) depends upon a relative comparison of impact velocity ratio (IVR) measurements for the same bone in the same patient over time.

An alternate methodology takes advantage of standardized impact velocity ratios (IVR) or bone impact reaction values, yet to be determined, for patients and bones having various characteristics such as age, sex, fitness level, bone type. Using this alternate method, a particular patient's bone impact reaction or impact velocity ratio (IVR) measurement may be compared to the standardized values in order to determine their potential for having osteoporosis. As I recently developed the present invention, there has not been an opportunity to determine these standardized values. However, it is believed to be a straightforward matter for one of ordinary skill in the art to use the present invention and measure a statistically significant group of individuals in order to determine these standardized values and the particular factors important in differentiating members of the group and to determine the amounts of medically significant changes that will lead to said differentiation.

While in the above description the bone was the subject of testing, the same method can be used to test the structural integrity of other biological tissues, such as the teeth and other materials or combination thereof, such as the integrity of the interface of metallic or composite medical implants into biological tissues or the medical implants themselves or critical parts of structures.

While the principal advantages and features of the present invention have been described above, a more complete and thorough understanding of the invention may be attained by referring to the drawings and description of the preferred embodiment which follow.

BRIEF DESCRIPTION OF THE SEVERAL VIEWS OF THE DRAWINGS

Further objects and features of the present invention are revealed in the following Detailed Description of the Preferred Embodiment of the invention and in the drawing figures wherein.

DETAILED DESCRIPTION OF THE INVENTION

Figure 1:
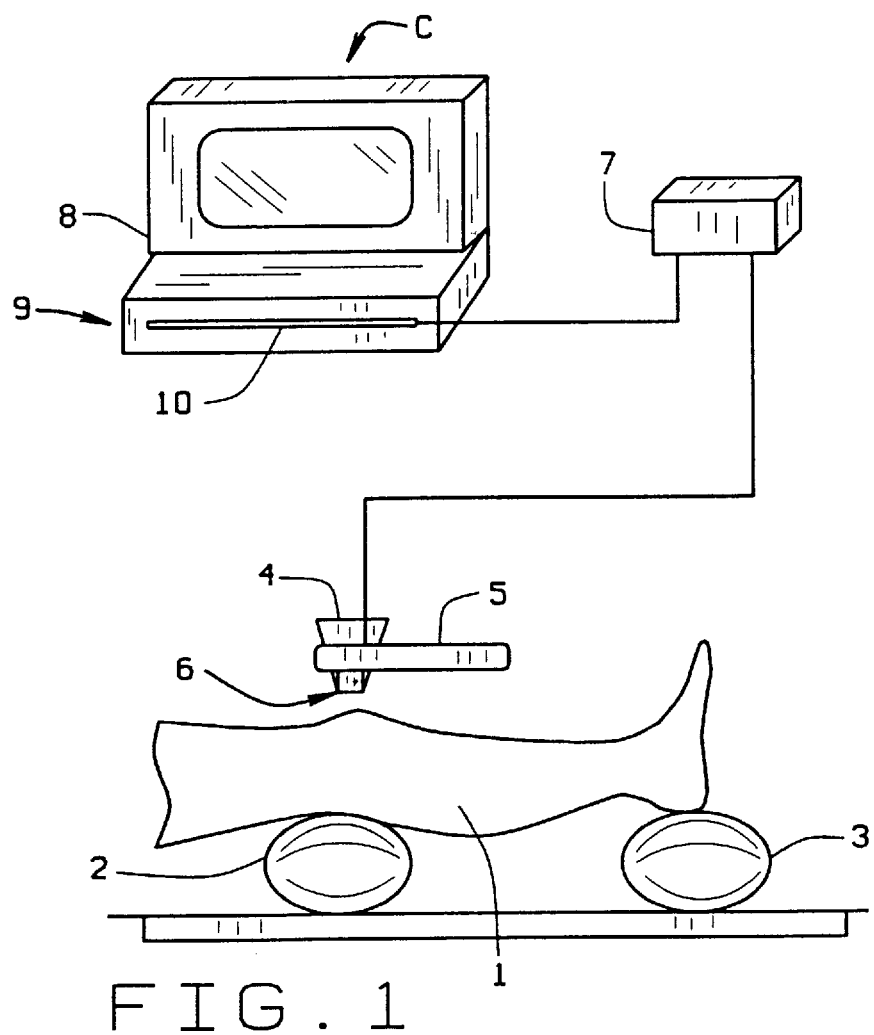
FIG. 1 is a diagrammatic view of a first technique for measuring the impact velocity ratio (IVR) as a monitor of the impact reaction by impacting the material with a speeding mass, in this embodiment an instrumented medical hammer, and electronically measuring the maximum velocities of approach and of rebound, the impact velocity ratio being defined as the ratio of the maximum rebound velocity right after the impact over the maximum velocity of approach right before the impact.
Figure 1A:
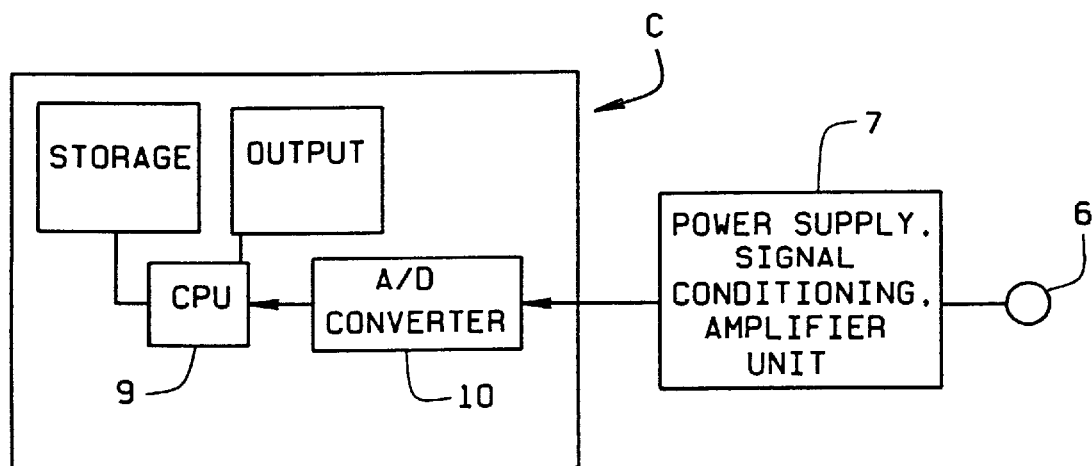
FIG. 1A is a block diagram of the apparatus of FIG. 1 for measuring the impact velocity ration (IVR)

As shown in FIG. 1 the inventor's first technique for measuring the material impact velocity ratio (IVR) as a monitor of the material impact reaction includes the step of inducing impact of a small medical hammer with a measured mass on the material which is desired to be measured, for example by striking the proximal end of a patient's tibia 1, which may be supported for convenience by a pair of very soft supports 2 and 3, with the instrumented medical hammer 4 head through the handle 5. A motion transducer 6, such as an accelerometer or a velocity transducer, in a preferred embodiment the accelerometer No 4374 manufactured by the Bruel & Kjaer Company of Marlborough, Mass., is affixed permanently on the hammer 4. The transducer 6 is powered by a power supply and signal conditioning and amplifier unit 7, in the preferred embodiment the conditioning amplifier No 2636 manufactured by the Bruel & Kjaer Company, that receives the electric signal from the transducer and transforms it by electronic means, well-known in the art, and it produces an output in the form of an electric signal proportional to the velocity of the hammer. The output is transferred to a data acquisition and recording system C, which in the preferred embodiment will consist of a computer screen 8, a central processing unit, a memory, a mass storage device and input-output devices, all integrated into a personal computer 9, such as for example, TM5000 computer notebook manufactured by the Texas Instruments Company, that includes an Analog to Digital Converter card 10, which may be in the preferred embodiment a part of a sound system of the computer 9. The signal is digitized in the card 10 and then transferred to computer 9 to compute the impact velocity ratio (IVR) and the results are stored in the mass-storage device of computer 9 and printed on the computer screen 8 in a form shown in FIG. 3.

Figure 2:
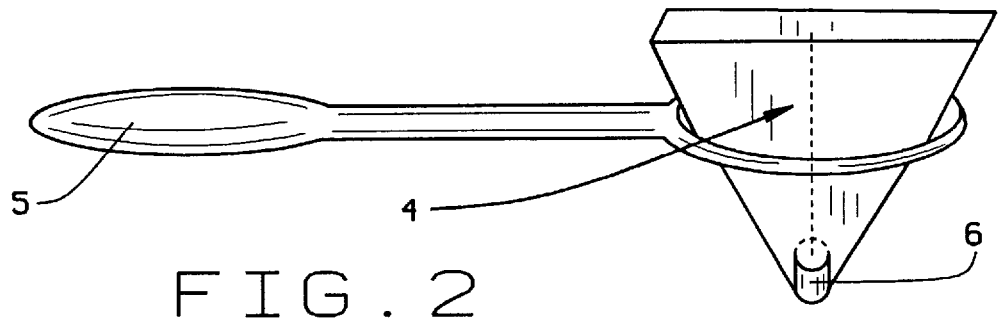
FIG. 2 is a view of the instrumented medical hammer used in the first preferred embodiment of the invention.

FIG. 2 shows the instrumented medical hammer in the preferred embodiment. It consists of a head 4 of triangular shape at the tip of which the transducer 6 is embedded and the cable connecting the transducer to the power supply 7 is flexible enough so that it will not interfere with the motion of the medical hammer head 4.

Figure 3:
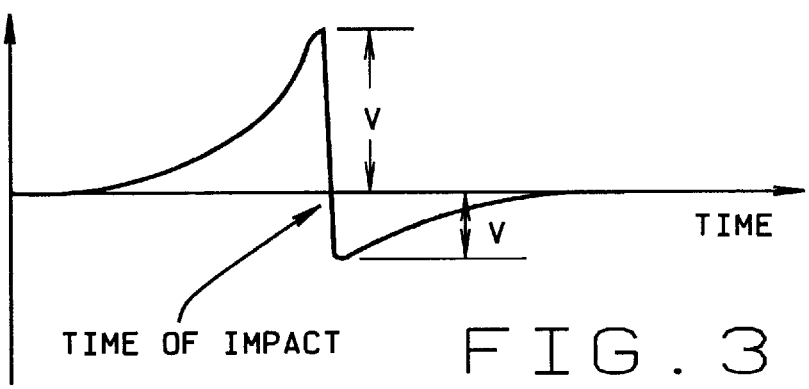
FIG. 3 is the time history of the impact hammer velocity and its reversal at the time of impact and during the period of rebound.

FIG. 3 shows a graph of the velocity of the head of the medical hammer 4 as a function of time, as it is recorded during the experiment on the screen 8 of the computer 9. As the person that performs the test is forcing the medical hammer to move towards the bone, he or she applies a force on the mass of the head 4 trough the handle 5. Due to this force, the head 4 accelerates and its velocity increases. Just prior to the time of impact, the magnitude of the approach velocity of the impact hammer 4 has a maximum value, V, because the impact decelerates the mass of the head 4 until it brings it to a complete stop and then the motion is reversed as the hammer head rebounds. Thus after the impact the velocity is reversed and the head 4 is accelerated again under the force that the compressed bone and surrounding tissue applies on the hammer. At the time of separation of the hammer 4 and transducer 6 from the bone and the surrounding tissue, the rebound velocity has a maximum value, v, because it is decelerated afterwards. The magnitude of this maximum rebound velocity, v, smaller than the maximum approach velocity V. During impact, the bone itself is accelerated during a short period of time to an unknown instantaneous velocity. This is because it is mounted on resilient support and it has its-own elasticity. The mass of the impact hammer 4 is m and the mass of the bone 1 is M. The impact velocity ratio (IVR) is $$\lambda = \left| \frac{v}{V} \right| = \left| \frac{e - m/M}{1 - m/M} \right| \tag{1}$$

where e is the restitution coefficient, which is a measure of the energy loss during impact, as it is well-known (see, for example: Housner, G. W., Hudson, D. E., *Applied Mechanics-Dynamics*, D. Van Norstand Co., New York, 1950). For non-perfectly elastic solids the restitution coefficient is always less than 1. The more it deviates from the value 1, the less integrity the material has. Moreover, reduced bone impact reaction means smaller mass M and it is clear that the impact velocity ratio (IVR) is reduced both by reduction in bone mass M and by increase of the energy absorption by the bone during impact due to the reduced resistance to impact. Energy absorption increases with decreasing modulus of elasticity and increasing material inelasticity, both conditions related with the loss of the ability of the bone to react to impact. It is seen that the impact velocity ratio (IVR) includes all the factors that effect reduced impact reaction thus it is superior to using separate measurements of mass density or modulus of elasticity or inelasticity or vibration damping to diagnose reduced structural integrity and osteoporosis.

Since the monitoring of the tissue impact reaction is done by observing changes, from equation (1) and for small changes of the observed parameters, namely the change in coefficient of restitution $\Delta e$ and the change in tissue mass $\Delta M$, we obtain $$\Delta\lambda = \frac{\Delta e}{1-r} + r(1-e)\frac{\Delta m}{M(1+r^2)} \tag{2}$$

where $r=m/M$, the ratio of the impact mass over the tissue mass.

For a small impact mass, $m<<M$ and $r<<1$. Therefore, Equation (2) takes the form:

$$\Delta\lambda = \Delta e + r(1-e)\frac{\Delta M}{M} \tag{3}$$

We observe that the change in $\lambda$ is the weighted addition of the change of the restitution coefficient and the change in bone mass, both becoming smaller if the bone looses mass in the form of voids, as in the case of osteoporosis.

It is possible from the impact velocity ratio to determine both the restitution coefficient and the mass of the stricken body, in this case the mass of the tissue under testing M if we run two tests with two different striking masses $m_1$ and $m_2$ that result, in general, in two different impact velocity ratios $\lambda_1$ and $\lambda_2$. Indeed using equation (1) and performing algebraic operation, one can obtain the following equations for the determination of the restitution coefficient e and the mass of the stricken body M:

$$k = \frac{1-\lambda_1}{1-\lambda_2}\frac{m_1}{m_2} \tag{4}$$

$$e = \frac{\lambda_1 - \lambda_2}{1-k}$$

$$M = \frac{(1-\lambda_1)m_1}{e-\lambda_1}$$

where k is an intermediate constant.

Finally, for infinite bone mass ($M>>m$) or if the mass M is rigidly attached to the ground, it is seen from the defining equation (1) above that impact velocity ratio $\lambda$ equals the coefficient of restitution, $\lambda=e$.

Figure 4:
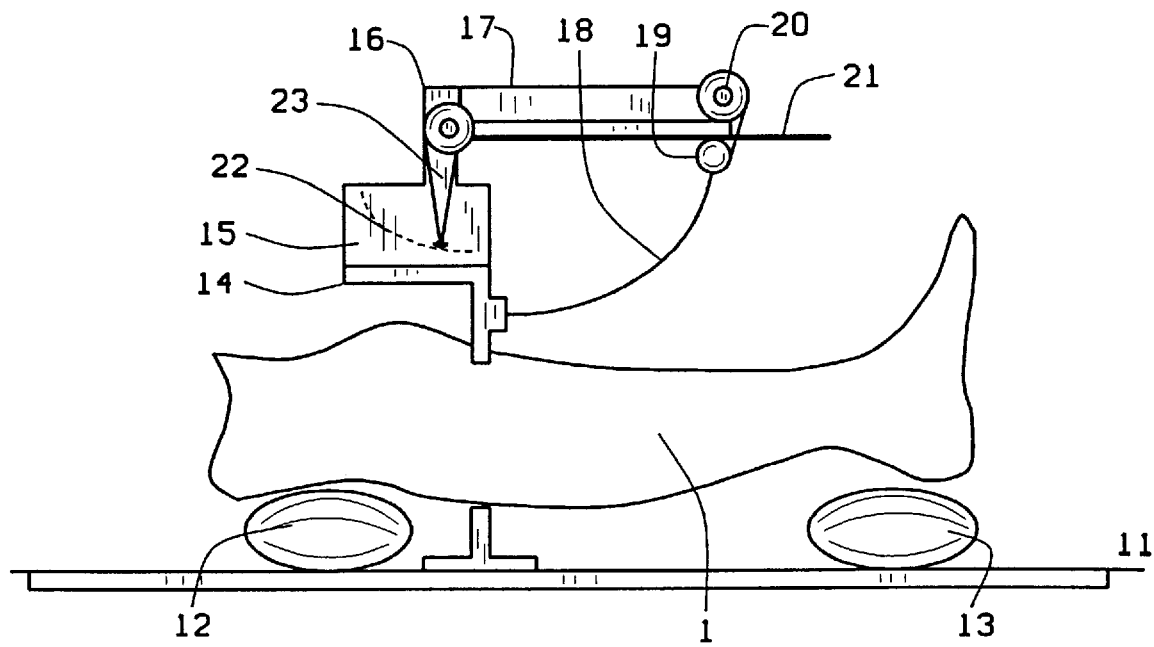
FIG. 4 is a diagrammatic view of a second technique for measuring the impact velocity ratio (IVR) as a monitor of the material impact reaction by impacting the material with a speeding mass through an actuator, for example a spring release in the preferred embodiment, and measuring the maximum displacement or velocity of impact and the maximum displacement or velocity of rebound.

As shown in FIG. 4, an alternate technique for measuring impact velocity ratio (IVR) may be used. As before, the patient's bone, such as the tibia 1, may be mounted for convenience on a rigid base 11 by soft support blocks 12 and 13. A support bracket 14 is securely mounted on the rigid base 11. On the bracket 14, another block 15 is mounted. On block 15, two brackets 16 and 17 are rigidly attached and at the right end of bracket 17 a ratchet wheel 20 is attached. On bracket 14 the left end of a leaf spring 18 is rigidly mounted, the right end has the form of a mass, in the preferred embodiment a small sphere 19. The sphere 19 is held in the uppermost place shown in FIG. 4 by the ratchet wheel 20. Rotation of the ratchet wheel 20 counter-clockwise releases the sphere 19 which under the force applied by the spring 18 starts speeding towards the bone. When it reaches the bone, it rebounds but it cannot reach the starting position due to an impact velocity ratio (IVR) less than 1.

The motion of the sphere 19 can be recorded electronically or mechanically. In one possible embodiment, a flat follower arm 21 follows the motion of the sphere 19 and the angular location of the follower arm can always be read on the scale 22 through pointer 23. Initially, the angle $\theta_1$ is measured on the scale 22 when the sphere 19 is forced manually to touch the surface of the tibia. Then the sphere 19 is raised manually so that it will latch with the ratchet mechanism 20. The angle $\theta_2$ of the follower 21 is recorded on the scale 22 at this position. Then the ratchet wheel is turned counter-clockwise to release the sphere 19. The sphere 19 speeds towards the tibia from the force of the spring 18 and rebounds after contacting or impacting on the tibia (or the tissue surrounding the tibia). The maximum rebound angle $\theta_3$ of the follower 21 is recorded on the scale 22. The impact velocity ratio (IVR) can be calculated as the ratio $$\lambda = (\theta_3 - \theta_1)/(\theta_2 - \theta_1). \tag{5}$$

Measurement of the angles $\theta_1$, $\theta_2$, $\theta_3$ or the corresponding displacements $x_1$, $x_2$, $X_3$ from the undeflected position of the spring 18 or the maximum impact and rebound velocities of the mass 19 can be also preformed with a variety of other known methods. The kinetic energy of the speeding mass before impact is proportional to the square of the velocity of approach before impact and equals the potential energy stored in the spring before release. The kinetic energy of the speeding mass right after impact is proportional to the square of the velocity of rebound right after impact and it equals the potential energy stored in the spring at its maximum deviation after impact. The potential energy of elastic deformation of the spring is proportional to the square of its deflection. Thus, the bone impact velocity ratio (IVR) is equal with the ratio of the maximum deviation after the impact over the initial deviation before the impact.

The inventor has conducted extensive experiments which prove the efficacy of utilizing the impact velocity ratio (IVR) for measuring bone impact reaction. In a first experiment, bovine femoral bones were treated in vitro with hydrochloric acid for varying lengths of time, their mass was measured, and then their impact velocity ratio (IVR) was determined using techniques similar to those disclosed herein. Their impact velocity ratios (IVR) were then compared with the impact velocity ratio (IVR) of the same femoral bones before the acid treatment. The impact velocity ratio (IVR) directly correlated with the number of hours of acid treatment of the bones and with the resulting bone density. This was to be expected as the longer the bones were immersed in the acid, the greater their porosity, the greater the reduction in their mass and hence the greater the reduction in their impact reaction. Furthermore, the change of the impact velocity ratio (IVR) was substantially greater than the change in the measured mass density of the bone. Hence, the impact velocity ratio (IVR) was considered to be highly sensitive to changes in impact reaction and thus a good parameter for measuring impact reaction as smaller changes in impact reaction could be readily detected.

There are various changes and modifications which may be made to the invention from those skilled in the art. These changes of different embodiments, however, are included in the teaching of the disclosure and it is intended that the invention be limited only by the scope of the claims that follow.

What is claimed is:

1. A measuring device for non-invasively determining the loss in density of a discrete piece of biological tissue, said device comprising:

a striking mass of known mass for impacting the said tissue, said striking mass having a maximum approach velocity V prior to impacting said tissue and a maximum rebound velocity v after impacting said tissue; and means for determining an impact velocity ratio v/V of the maximum rebound velocity to the maximum approach velocity, the impact velocity ratio being indicative of the density of the tissue struck.

2. The measuring device of claim 1 wherein in the striking mass is an instrumented medical hammer, the hammer including a handle and a head, said head having an impact zone; said determining means including:

a motion transducer mounted in the hammer head, said transducer sensing the approach velocity of the mass of the medical hammer prior to impact with the tissue and the rebound velocity of the mass of the medical hammer after impact with said tissue; the transducer generating a signal indicative of said approach and rebound velocities;

a computer which receives said signal from said transducer, said computer determining the maximum approach velocity and the maximum rebound velocity, and from said velocities, said computer determining the impact velocity ratio (IVR).

3. The measuring device of claim 2 including an output device, said output device generating an image indicative of the speed history of the hammer and outputting the impact velocity ratio.

4. The measuring device of claim 2 including a signal amplifier which receives said signal from said transducer to amplify said transducer signal, said amplifier generating an amplified signal, said computer receiving said amplified signal.

5. The measuring device of claim 4 including an analog-to-digital converter, said converter receiving said amplified signal and generating a converted signal, said computer receiving said converted signal.

6. The measuring device of claim 2 wherein said transducer measures the maximum instantaneous velocity of a hammer just before it contacts said tissue and the instantaneous velocity of said hammer just as said hammer separates from the tissue after rebound.

7. The device of claim 6 including a recorder for recording the instantaneous velocity of a medical hammer just before it contacts a tissue through the surrounding soft tissue and the instantaneous velocity of said hammer just as the hammer separates from the tissue after rebound.

8. The device of claim 1 including an actuator, said striking mass being attachable to said actuator to be held by the actuator, said actuator being selectively switchable between a first mode in which said actuator holds the striking mass in a ready position to be released to strike and tissue and a second mode in which said actuator releases said striking mass to allow said striking mass to strike said tissue;

a measuring device for measuring an initial displacement D1 of said striking mass when said actuator is in said first mode prior to release of said striking mass, a displacement D2 of said striking mass when it strikes said tissue, and a maximum displacement D3 of the striking mass after it rebounds from said tissue;

the impact velocity ratio (IVR) being equal to (D3–D2)/(D1–D2).

9. The device of claim 8 including:

a base;

a frame having a first part extending upwardly from said base and a second part extending from said first part over said base;

a resilient spring arm having a first end connected to said frame first part below said frame second part and a distal end extending outwardly to be positioned over said tissue, said striking mass being mounted to the end of said spring arm;

said actuator being mounted to said frame second part, said actuator being operable to hold said striking mass and to release said striking mass;

whereby, when said actuator is operated to release said striking mass, said spring arm forces said striking mass to move toward said tissue to impact said tissue.

10. The device of claim 9 wherein said measuring device determines the angular position of said striking mass relative to said frame, the displacement D1 corresponding to the angular position of said mass when said mass is being held by said actuator, the displacement D2 corresponding to the angular position of said mass when said mass strikes said tissue, and the displacement D3 corresponding to the angular displacement of said mass upon reaching a maximum rebound height.

11. The device of claim 10 wherein the measuring device includes a follower arm pivotally connected to said frame, said follower arm riding on said striking mass as said striking mass moves toward and away from said tissue; and a scale which measures the angular position of said follower arm throughout the movement of said mass.

12. The device of claim 11 wherein said follower arm has a first end which is pivotally connected to said frame, said device including a pointer fixed to said follower arm free end and which points to said scale.

13. A device for determining a impact reaction of a striking mass when forced against a stricken mass, said striking mass being made of a material such that the striking mass will rebound when it impacts said stricken mass; said device comprising:

an actuator, said actuator being selectively switchable between a first mode in which said actuator holds said striking mass and a second mode in which said actuator releases said striking mass to allow said striking mass to impact said stricken mass; and a sensor connected to said striking mass for determining the instantaneous position of said mass;

said impact reaction being a ratio of the maximum height to which said striking mass rebounds to the initial height from which said striking mass is released.

14. The device of claim 13 wherein the stricken mass is a discrete piece of medical implant.

15. The device of claim 13 wherein the stricken mass is a piece of biological tissue.

16. The device of claim 13 wherein said sensor measures:

the initial displacement (D1) of the mass before it is released to impact the stricken mass;

the maximum impact location displacement (D2) of the striking mass at the time of impact with the stricken mass;

and the final maximum displacement (D3) of the striking mass as it moves away from the said stricken mass; said impact reaction being equal to the ratio of (D1–D2)/(D3–D2).

17. The device of claim 16 including a follower arm pivotally connected to said frame, said follower arm riding on said striking mass as said striking mass moves toward and away from said stricken mass; and a scale which measures the angular position of said follower arm throughout the movement of said striking mass; said follower arm having a first end which is pivotally connected to said frame, said measuring device including a pointer fixed to said follower arm free end and which points to said scale.

18. A method for determining the density of a tissue or bone, the method comprising the steps of:

striking the tissue or bone with a striking mass and allowing the striking mass to rebound from the stricken mass; and determining an impact ratio, the impact ratio being indicative of the density of the tissue or bone.

19. The method of claim 18 wherein the stricken mass comprises a medical implant positioned within the hard or soft tissue in an organism, the impact ratio being indicative of the structural integrity of the implant.

20. The method of claim 18 wherein the stricken mass is bone, the impact ratio being indicative of the density of the bone; the method further comprising comparing the impact ratio determined against standardized impact ratio data to diagnose the onset of osteoporosis.

21. The method of claim 18 including wherein the striking mass is releasably held in a frame, the step of determining the impact ratio includes:

measuring an initial displacement D1 of the striking mass before it is released to strike the stricken mass;

measuring an maximum impact location displacement D2 of the striking mass when said striking mass impacts the stricken mass; and measuring the maximum rebound displacement D3 after said striking mass impacts said stricken mass;

said impact ratio being equal to (D1–D2)/(D3–D2).

22. The method of claim 18 wherein said step of determining the impact ratio comprises measuring the maximum approach velocity $V_a$ prior to impact of the striking mass with the stricken mass and measuring the maximum rebound velocity $V_r$ after said striking mass impacts the stricken mass, the impact ratio being equal to $V_a/V_r$.

23. A method for non-invasively diagnosing osteoporosis, the method comprising the steps of:

striking a bone of a patient through the tissues surrounding the bone with a predetermined mass;

allowing the striking mass to rebound from the bond; and measuring the impact ratio of the mass as it impacts a bone of the patient;

comparing said impact ratio with a plurality of predetermined impact ratios of healthy patients;

determining if a difference exists between said measured impact ratio and said predetermined impact ratios in medically significant amounts which will indicate the deterioration of the bone impact reaction and onset or degree of osteoporosis, in the absence of other medically significant causative factors.

24. The method of claim 23 including wherein the striking mass is releasably held in a frame, the step of determining the impact ratio includes:

measuring an initial displacement D1 of the striking mass before it is released to strike the bone;

measuring an maximum impact location displacement D2 of the striking mass when said striking mass impacts the bone; and measuring the maximum rebound displacement D3 after said striking mass impacts said bone;

said impact ratio being equal to (D1–D2)/(D3–D2).

25. The method of claim 23 wherein said striking mass is a medical hammer, said hammer including a transducer for monitoring the speed of the hammer; the step of determining the impact ratio comprising measuring the maximum approach velocity $V_a$ of the hammer prior to impact of the bone with the hammer and measuring the maximum rebound velocity $V_r$ of the hammer after the hammer impacts the bone, the impact ratio being equal to $V_a/V_r$.

26. The method of claim 23 wherein comparing step includes comparing said measured impact ratio with a plurality of predetermined impact ratios of standardized categories of patients and bones having various characteristics such as age, sex, fitness level, bone type.

27. A method for determining the structural integrity of a stricken mass, the method comprising the steps of:

striking the stricken mass with a striking mass and allowing the striking mass to rebound from the stricken mass; and determining an impact ratio, the impact ratio being indicative of the structural integrity of the stricken mass.

28. The method of claim 27 wherein the stricken mass comprises a structural part positioned within the hard or soft tissue in an organism, the impact ratio being indicative of the structural integrity of the structural part.

* * * * *

UNITED STATES PATENT AND TRADEMARK OFFICE
CERTIFICATE OF CORRECTION

PATENT NO. : 5,836,891
DATED : November 17, 1998
INVENTOR(S) : Andrew D. Dimarogonas It is certified that error appears in the above-identified patent and that said Letters Patent is hereby corrected as shown below:

Please insert the following claim into this patent:
-- 29. The device of claim 15 including:
    a base upon;
    a frame having a first part extending upwardly from said base and a second part extending from said first part over said base;
    a resilient spring arm having a first end connected to said frame first part below said frame second part and a distal end extending outwardly from said frame first part to be positioned over said stricken mass, said striking mass being mounted near the distal end of said spring arm;
    said actuator being mounted to said frame second part, said actuator being operable to hold said striking mass and to release said striking mass;
    said sensor including a scale for determining the angular position of said striking mass as it moves towards and away from said stricken mass, the displacement D1 corresponding to the angular position of said striking mass when said striking mass is being held by said actuator, the displacement D2 corresponding to the anglar position of said striking mass when said striking mass strikes said stricken mass, and the displacement D3 corresponding to the angular displacement of said striking mass upon reaching a maxium rebound height after impact with said stricken mass. --

Claim 17, column 10,
Line 59, change "16" to -- 29 --.

Signed and Sealed this

Thirtieth Day of October, 2001

Attest:

NICHOLAS P. GODICI
Attesting Officer     Acting Director of the United States Patent and Trademark Office